United States Patent
Erdelmeier et al.

(10) Patent No.: US 6,241,988 B1
(45) Date of Patent: *Jun. 5, 2001

(54) STABLE EXTRACT OF HYPERICUM PERFORATUM L., A METHOD FOR PRODUCING THE SAME, AND CORRESPONDING PHARMACEUTICAL PREPARATIONS

(75) Inventors: Clemens Erdelmeier, Karlsruhe; Eckhart Grethlein, Pfinztal; Friedrich Lang, Hagenbach; Rainer Oschmann, Landau; Karl-Heinz Stumpf, Karlsruhe, all of (DE)

(73) Assignee: Dr. Willmar Schwabe GmbH & Co., Karlsruhe (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/402,739

(22) PCT Filed: Apr. 7, 1998

(86) PCT No.: PCT/DE98/01003

§ 371 Date: Feb. 18, 2000

§ 102(e) Date: Feb. 18, 2000

(87) PCT Pub. No.: WO98/44936

PCT Pub. Date: Oct. 15, 1998

(30) Foreign Application Priority Data

Apr. 8, 1997 (DE) .............................................. 197 14 450

(51) Int. Cl.[7] .................................................. A61K 35/78

(52) U.S. Cl. ........................................................ 424/195.1

(58) Field of Search ......................... 424/195.1; 426/541; 514/783

(56) References Cited

U.S. PATENT DOCUMENTS

| | | |
|---|---|---|
| 4,178,372 | 12/1979 | Coats . |
| 4,446,131 | 5/1984 | Maughani . |
| 5,578,307 | * 11/1996 | Wunderlich et al. . |

FOREIGN PATENT DOCUMENTS

| | | |
|---|---|---|
| 2 101 888 | 1/1983 | (GB) . |
| 79428 | * 12/1980 | (RO) . |

OTHER PUBLICATIONS

Moyler, D. A., Flavour and Fragrance Journal, vol. 8, 235–247. Extraction of essential oils with carbon dioxide, 1993.*

Maisenbacher et al. Planta Med, vol. 58 (4), 351–354. Analysis and stability of Hyperici oleum, 1991.*

H. Finzelberg's Nachfolger GmbH & Co KG, Batch documentation (batch 1565931, article 0 155610) for oleum hyperici olive base oil (printout dated Apr. 20, 1999) (English translation).

H. Finzelberg's Nachfolger GmbH & Co KG, internal specification for preparation of Oleum mac. Hyperici e flor. based on olive oil (patent extract) (English translation).

H. Finzelberg's Nachfolger GmbH & Co KG, Result of Analysis 99–15 Preparation of Hypericum extracts with and without stablizers/test of Hyperforin stability (English translation).

H. Finzelberg's Nachfolger GmbH & Co KG, Stability of Hyperforin in Hypericum extracts according to example 2 of DE 196 19 512 (Apr. 14, 1999) (English translation).

H. Finzelberg's Nachfolger GmbH & Co KG validating report (excerpt) for Hypericum total extracts; extracting agent 60% EtOH (m/m) (Apr. 20, 1999) (English translation).

H. Finzelberg's Nachfolger GmbH & Co KG, Hyperforin contents in Finzelberg's Hypericum extracts—long–term values (Nov. 16, 1998) (English Translation).

Pharm Stoffliste, Properties and use of ascorbic acid (not dated), pp. 314–315 (English translation and copy of German document).

Ph.D. thesis of Maisenbacher, pp. 6–15 (English translation of relevant portions of pp. 7, 11, 13, 14 and 15, and German document).

Ph.D. thesis of Maisenbacher, pp. 15 and 269. Other ingredients. (German version).

Citation #93 from p. 269 of Ph.D, thesis of Maisenbacher (English translation).

H. Finzelberg's Nachfolger GmbH & Co KG, Hyperforin contents in St. John's wort fresh plant $CO_2$ extracts (Nov. 16, 1998) (English translation).

H. Finzelberg's Nachfolger GmbH & Co KG, Hyperforin contents in St. John's wort fresh plant $CO_2$ extracts (Apr. 16, 1999) (English translation).

H. Finzelberg's Nachfolger GmbH & Co KG, Preparation of various Hypericum extract according to example 1 of Schwabe's Patent No. EP 0 599 307 A1 (D4) as well as example 1 of DE 196 19 512 and subsequent stability testing (Aug. 23, 1999) (English translation).

H. Finzelberg's Nachfolger GmbH & Co KG GmbH & Co KG, Result of analysis No. 99–74, Preparation of Hypericum extracts with and without stabilizers/test of Hyperforin stability (English translation).

Gehrlicher GmbH & Co. KG, Stability of Hyperforin (Table 1A) (Enclosure 1). (English translation).

Gehrlicher GmbH & co. KG, Stability of Hyperforin (Table 1B) (Enclosure 1). (English translation).

Dr. Willmar Schwabe GmbH & Co., Stability of Hyperforin at room temperature in stabilized and non–stabilized Hypericum Extracts (D31) (German document and English translation).

(List continued on next page.)

Primary Examiner—Jean C. Witz
(74) Attorney, Agent, or Firm—McDonnell Boehnen Hulbert & Berghoff; Steven J. Sarussi

(57) ABSTRACT

Disclosed is an improved extract of *Hypericum perforatum* L. (St. John's wort) containing Hyperforin, in which the Hyperforin is stabilized against decomposition or degradation by means of a stabilizer.

31 Claims, No Drawings

OTHER PUBLICATIONS

Dr.Willmar Schwabe GmbH & Co. Table 1. Content and stability of Hyperforin in preparations of St. John's Wort (D32) (German document and English translation).

Ullmann's Encyclopedia of Industrial Chemistry, vol. A 10, p. 288–289 (D4 EP I), VCH Verlagsgesellschaft mbH, Weinheim, Germany, 1987.

Dr. Willmar Schwabe GmbH & Co., Comparison of Hyperforin stability in non–stabilized $CO_2$ extracts from fresh plant and drug (D 25) (German document and English translation).

Herbert P. Fiedler, Lexikon der Hilfsstoffe (Dictionary of Adjuvants), (D3EPI) $4^{th}$ Edition (1996), pp. 201–202 and p. 601 (German document and English translation of pp. 201–202).

Römpp Chemie Lexikon (Römpp Chemical Dictionary), $9^{th}$ Edition (1990), p. 1373, Characteristics and Uses of Flavones, (D3EPIII/IV) (English translation and German document).

R. Hänsel et al.: *Drogen E–O* [Drugs E–O], Springer–Verlag, Berlin 1993, vol. 5, pp. 474–495 (English translation of portions of pp. 474–476, 479 and 481–483, and German document).

"Arzneipflanzen in der Sowjetunion" [Medicinal Plants in the Soviet Union], Reports of the Institute for East Europe at the Free University of Berlin; vol. 44; pp. 134–138, Berlin, 1996 (Ref. 34 cited at p. 483 of R. Hänsel document, above. German document and English translation of part of p. 134).

Pharmazeutische Zeitung No. 46, vol. 139, Nov. 17, 1994, pp. 3959–3977 (English translation of Summary section and "Phloroglucin derivatives" section on p. 3962, and copy of German document).

Deutsche Apohteker Zeitung, vol. 138, No. 1/2, Jan. 8, 1998, p. 57 (English translation and copy of German document).

Pharmazeutische Zeitung, No. 24, vol. 144, Jun. 17, 1999, pp. 1946–1957 (English translation and copy of German document).

J. Hölzl et al., Planta Med., vol. 55, (1989), pp. 601–602.

Pharmacopsychiatry, Supplement 1, vol. 31, Jun. 1998, pp. 1–60.

Von Renate Berghöfer and Josef Hölzl, Johanniskraut (hypericum perforatum L.), Deutsche Apotheker Zeitung, 126, Jahrg. Nr. 47, Nov. 20, 1986, pp. 2569–2573. (German document and English translation).

Gehrlicher GmbH & Co., KG, Instability of Hyperforin at room temperature (Enclosure 2) (English translation).

\* cited by examiner

STABLE EXTRACT OF HYPERICUM PERFORATUM L., A METHOD FOR PRODUCING THE SAME, AND CORRESPONDING PHARMACEUTICAL PREPARATIONS

It is proved by pharmacological and clinical trials that extracts of St. John's wort (extracts of Hypericum) can be successfully used in case of light to moderately severe depressions. The mild anti-depressive overall effect could not be exactly assigned to one or several components; cf. J. Hölzl, S. Sattler and H. Schütt, Johanniskraut: Eine Alternative zu synthetischen Antidepressiva (St. Johns wort: an alternative to synthetic antidepressants), *Pharmazeutische Zeitung*, No. 46, 139. Jahrgang, 17. November 1994, pages 3959–3977 and E. Steinegger and R. Hänsel, Pharmakognosie, 5$^{th}$ edition 1992, pages 672–674, Springer Verlag. However, recently there are stronger hints that Hyperforin provides a considerable contribution to achieve effectiveness (EP-A-0 599 307).

The crude herbal drug consists of the aerial parts of *Hypericum perforatum* L. The components of *Hypericum perforatum* L. are among others Hypericin and Hyperforin; cf. J. Hölzl et al., see above.

The preparation of extracts of Hypericum with an enriched content of Hypericin is described in DE-PS- 1 569 849 as well as in S. Niesel and H. Schilcher in *Arch. Pharm.*, Vol. 323 (1990), page 755.

From R. Berghöfer and J. Hölzl, *Deutsche Apothekerzeitung*, Vol. 126, No. 47 (1986) pages 2569–2573, it is known that Hyperforin in extracts from stored crude herbal drugs is already completely degraded after one week whilst it should be more stable in the extract of fresh plants. These authors assume that fresh plants contain a stabilizer for Hyperforin.

J. Hölzl et al., *Planta Med.*, Vol. 55 (1989) pages 601–602 report about Hypericum oil and assume a correlation between the concentration of Hypericin and the peroxide value. Hypericum oil products exposed to the sun light show different peroxide values. But according to J. Hölzl et al., there is no relation between the peroxide value and the concentration of Hypericin.

P. Maisenbacher and K. -A. Kovar report in *Planta Med.*, Vol. 58, (1992), pages 351 to 354 about the stability of Hypericum oil. This oil also contained Hyperforin which was degraded within a few weeks.

From EP-A- 0 599 307 primary extracts of the crude herbal drug of St. John's wort (see examples 1–3) are known. These primary extracts are obtained by simply extracting the crude herbal drug with 96% and 60% aqueous ethanol, respectively without any precautionary measures and without any additions.

In example 1 the Hyperforin content of the [fresh] primary extract is stated to be 6.3%. In the two other examples no Hyperforin content is stated at all. We have found that such Hyperforin extracts are extremely unstable; see description, example 5, Table I. The primary extract obtained according to example 1 (comparison) by extraction of the drug with 70% aqueous ethanol contains after 13 weeks no longer any detectable amounts of Hyperforin.

Furthermore, it is known to prepare Hypericum oil (oil of St. John's wort; *Oleum hyperici*) by extraction of crushed (mashed) fresh flowers of St. John's wort with a fatty oil such as olive oil, soya-bean oil, wheat germ oil or sunflower seed oil. Hypericum oil contains variable amounts of Hyperforin and is useful for the topical treatment of wounds, in particular burns and abrasion; cf. P. Maisenbacher and K. -A. Kovar, *Planta Med.*, Vol. 58 (1992), pages 351–354 and J. Hölzl, L. Demisch and S. Stock, *Planta Med.*, Vol. 55 (1989), pages 601–602.

As well in the drug as in conventional extracts of Hypericum the content of Hyperforin decreases dramatically until the disappearance of the substance within a few months on conventional storage; cf. Ph.D. thesis of P. Maisenbacher, Tübingen 1991 and the Ph.D. thesis of R. Berghöfer, Marburg/L. 1987. In earlier experiments with oily extracts of Hypericum the stability of compositions containing Hyperforin could only be improved in a better way by storage under Argon; cf. Ph.D. thesis of P. Maisenbacher, see above. A stabilisation with anti-oxidants such as butylhydroxytoluene (BHT) and butylhydroxyanisole (BHA) was not achieved in these extracts. Moreover, conventional anti-oxidants such as Oxynex LM and Oxynex 2004 do also not improve the stability. In case of Hypericum oil the best stability is achieved (according to P. Maisenbacher's Ph.D. thesis) by use of octyldodecanol (Eutanol G) as an extraction agent. On pages 154–155 Maisenbacher describes historical methods of preparation. The crude herbal drug is extracted with hot plant oil, sometimes under the addition of oil of turpentine. Also in this case Maisenbacher observed degradation, in particular under the influence of water. On pages 158–166 Maisenbacher describes the conditions for an optimal process of preparation. The following instructions are particularly revealing: water has to be kept out; Eutanol G should be used as extraction agent; conventional anti-oxidants provide now protection against oxidation. After an induction period of 3 weeks a steady degradation of the Hyperforines began for the olive oil extract; cf. FIGS. 7–10. Despite rinsing with inert gas a complete degradation occurred after 3 months; cf. page 160. The oil prepared by the use of Eutanol G is stable for half a year at ambient temperature under argon. At 30° C. slow degradation occurs; cf. page 161.

Extracts of Hypericum containing Hyperforin can be prepared with pharmaceutically conventional inorganic or organic solvents or mixtures thereof (P. List and P. C. Schmidt, Technologie pflanzlicher Arzneizubereitungen, Wissensch. Verlagsgesellschaft mbH, Stuttgart, 1984).

Conventional aqueous ethanolic extracts of Hypericum and finished pharmaceutical compositions prepared thereof usually contain less than about 1% Hyperforin (based on the extract). After the storage the value obviously decreases and moves towards zero depending on the individual storage conditions. One assumes that processes of oxidation are responsible for the degradation of the Hyperforin in the crude herbal drug and the extract.

The technical problem of the present invention is to provide Hyperforin-containing stabilized extracts of Hypericum perforatum L. (St John's wort) in which the Hyperforin remains stable. It is a further technical problem of the invention to provide a process for the preparation of these stabilized extracts as well as to provide pharmaceutical compositions containing these stabilized extracts in which the Hyperforin content also remains stable.

According to the present invention these technical problems are solved by extracts according to claims 1 to 8, by the process according to claims 9 to 21 as well as by the pharmaceutical composition according to claim 22.

The present invention is based inter alia on the unexpected result that an extract of Hypericum with certain anti-oxidant and/or oxygen binding stabilizers and reducing agents, which are able to degrade oxidants such as radicals, peroxides, atmospheric oxygen etc. in the extract and/or to inhibit the degradation of Hyperforin, and optionally carrying out the extraction under inert gas such as nitrogen and/or exclusion of light and/or with a solvent with a highly reduced oxygen content, is more stable than an untreated extract of Hypericum. This extract can be derived contrary to the obsevations made by R. Berghöfer and J. Hölzl (see above) from a dried and stored crude herbal drug.

A solvent with a highly reduced oxygen content can be prepared by physical treatment such as rinsing with an inert gas such as nitrogen. In case the extract of Hypericum is preserved or stabilized according to the present invention, in particular by addition of an anti-oxidant and optionally by exclusion of light and atmospheric oxygen, then the Hyperforin in this extract remains essentially stable. The protection against light and atmospheric oxygen can also be achieved by a corresponding pharmaceutical formulation.

In a preferred embodiment of the process of the present invention for the preparation of the stabilized extract the fresh or preferably dried drug of St. John's wort is extracted with aqueous ethanol, the oxygen content of which was highly reduced by physical treatment. To the extract solution an anti-oxidant agent as a stabilizer is added and dissolved therein because of possibly present oxidants. Further examples for preferred solvents for the extraction of St. John's wort comprise aqueous methanol, alkanes with low boiling points having about 5 to 8 carbon atoms such as pentanes, hexanes and heptanes, in particular n-heptane, and liquid or supercritical carbon dioxide. The term "aqueous methanol or ethanol" denotes methanol or ethanol having a water content of preferably up to about 40% by volume.

Particular examples for preferred anti-oxidant stabilizers or anti-oxidant agents are pharmacologically acceptable substances, able to inhibit the degradation of Hyperforin and/or to reduce oxidants in the extract or the pharmaceutical composition. Particular examples are organic thiol compounds, such as cysteine and glutathione, as well as ascorbic acid and derivates thereof such as the fatty acid esters of ascorbic acid, such as the myristate, palmitate and stearate.

The anti-oxidant stabilizers are added to the extract preparation of Hypericum in an amount sufficient to stabilize the Hyperforin. In general concentrations from 0.01 to 5% anti-oxidant stabilizer based on the extract of Hypericum are sufficient.

In a further embodiment it will be proceeded as described above but the addition of the stabilizer is carried out at the stage after drying the extract solution, i.e. after stripping off the solvent.

In a further preferred embodiment of the invention the anti-oxidant stabilizer is added, at the stage of the finished pharmaceutical product, together with other pharmaceutical additives.

Preferably all embodiments are carried out under the exclusion of light and oxygen.

The obtained extracts can be processed together with conventional pharmaceutical additives, optionally after adding again a stabilzer to pharmaceutical compositions, such as capsules, film tablets and coated tablets.

Pharmaceutical additives are fillers, binding agents, disintegrants, lubricants and coating agents for film tablets and coated tablets, as well as oils and fats as fillers for soft gelatin capsules.

The present invention is explained by means of the following examples. Percentages are percents by weight if not otherwise stated. Nitrogen was used as an inert gas (protective gas). It should be noted that also other inert gases, such as argon or krypton can be used.

EXAMPLE 1 (COMPARISON EXAMPLE)

1 kg crude herbal drug of St. John's wort was finely milled in a mill and 7 kg 70(v/v)% ethanol was added. The suspension of 1 kg crude herbal drug and 7 kg solvent was intensively stirred at 55° C. for one hour under inert gas. Then the resulting extract was separated from the crude herbal drug by means of centrifugation. The residue of the drug was accordingly extracted for a second time with 7 kg solvent. The two extract solutions were combined and the dry residue in the extract was determined with an aliquot. The extract was gently concentrated under reduced pressure to a dry residue content of 72% and again dried at 40° C. under reduced pressure. 0.44 kg dry extract was obtained. The Hyperforin content was 0.37%.

EXAMPLE 2

8 kg crude herbal drug of St. John's wort was finely milled in a mill and 56 kg 70(v/v)% ethanol was added. The oxygen content of the used solvent was reduced before by means of rinsing with inert gas. The suspension of 8 kg crude herbal drug and 56 kg solvent was intensively stirred under inert gas at 55° C. for one hour. Then the obtained extract was separated from the drug by means of centrifugation while rinsing with nitrogen as an inert gas. The drug residue was extracted a second time in the same manner. The two extract solutions were combined and 0.1% ascorbic acid was added. The solution was intensively stirred for 10 minutes under nitrogen as inert gas and was then gently concentrated under reduced pressure to a dry residue content of 70% and again dried at 40° C. under reduced pressure. 2.52 kg stabilized dry extract with a Hyperforin content of 0.9% was obtained.

EXAMPLE 3

To 400 g dry, finely milled fresh St. John's wort 3.2 kg n-heptane were added. 12 mg ascorbic acid palmitate were added and the mixture was then extracted during one hour by permanent stirring at 50° C. under exclusion of light. Then the mixture was sucked off by means of a Seitz Supra 1500 Filter and the drug residue was extracted a second time in the same manner. The combined extract solutions were concentrated at 35° C. by means of a rotary evaporator under exclusion of light to a dry residue content of about 70% and than freeze-dried. 21 g dry extract was obtained with a Hyperforin content of 1.7%.

EXAMPLE 4

To 470 g dry, finely milled St. John's wort 15 mg of ascorbic acid palmitate were added and then the mixture was delivered into a high-pressure-extraction unit and extracted under 200 bar at 35° C. About 7.5 kg carbon dioxide was used. After the extraction, the pressure was reduced to 60 bar in order to separate the extract. The extract was removed from the unit and mixed with 10 mg ascorbic acid palmitate. 12.2 g dry extract with a Hyperforin content of 1.9% was obtained.

EXAMPLE 5

2.4 kg crude herbal drug of St. John's wort was milled in a mill and 16 kg 80(v/v)% methanol was added, which was rinsed with nitrogen before. This mixture was then stirred for one hour at 55° C. The obtained extract solution was separated from the drug residue by means of centrifugation. The residue of the drug was accordingly extracted for a second time. The two extract solutions were combined and 1.0% by weight ascorbic acid was added. This solution was stirred for 15 minutes. Then the extract solution was gently concentrated under reduced pressure to a dry residue content of 70% and then again dried at 40° C. under reduced pressure. 0.5 kg stabilized dry extract with a Hyperforin content of 0.7% was obtained. The content of total Hypericin in this extract was 0.46%.

EXAMPLE 6

Checking the stability of Hyperforin.

In this example the Hyperforin content of an extract according to Example 1 without particular precautionary measures and additions during the preparation was compared with extracts prepared according to Examples 2 to 5 of this invention. The extracts prepared in accordance with the present invention were stored under nitrogen and exclusion of light at room temperature. The results are summerized in Table I. The result shows a substantially unchanged Hyperforin content of the extracts prepared in accordance with the present invention after 6 months.

| dry extract | hyperforin | hyperforin content % | |
|---|---|---|---|
| Example | Initial content % | after 13 weeks | after 6 months |
| Example 1 | 0.37 | 0.0 | 0.0 |
| Example 2 | 0.9 | 0.9 | 0.88 |
| Example 3 | 1.7 | 1.7 | 1.68 |
| Example 4 | 1.9 | 1.9 | 1.89 |
| Example 5 | 0.7 | 0.7 | 0.63 |

EXAMPLE 7

Soft-gelatine capsules with an extract of Hypericum.

| Composition: | |
|---|---|
| dry extract of Hypericum | 300 mg |
| ascorbic acid | 0.25 mg |
| octyldodecanol | 200 mg |

Preparation:

The dry extract and ascorbic acid were dispersed together in octyldodecanol and processed under exclusion of atmospheric oxygen to soft-gelatine capsules.

EXAMPLE 8

Film tablet with extract of Hypericum.

| Composition: | |
|---|---|
| dry extract of Hypericum | 300 mg |
| cellulose | 100 mg |
| modified starch | 90 mg |
| Na-carboxymethylcellulose | 30 mg |
| highly dispersed siliciumdioxide | 5.0 mg |
| ascorbic acid | 5.0 mg |
| magnesium stearate | 5.0 mg |
| hydroxypropylmethylcellulose-coating | 20.0 mg |

Preparation:

The components were mixed in dry condition in a mixer and were directly pressed into tablets. The obtained tablets were coated with a coating of hydroxypropylmethylcellulose.

What is claimed is:

1. A stable extract of *Hypericum perforatum* L. (St. John's wort) with a Hyperforin content of 0.1% to 2%, wherein the extract comprises an amount of a stabilizer selected from the group consisting of organic thiol compounds, ascorbic acid, ascorbic acid derivatives, and mixtures thereof effective to stabilize the Hyperforin against decomposition or degradation.

2. An extract according to claim 1, wherein the stabilizer is present in a concentration of 0.01% to 5%, based on the extract.

3. An extract according to claim 1, wherein the stabilizer is present in a concentration of 0.2% to 1%, based on the extract.

4. An extract according to claim 1, wherein the stabilizer is cysteine.

5. An extract according to claim 1, wherein the stabilizer is glutathione.

6. An extract according to claim 1, wherein the stabilizer is ascorbic acid.

7. An extract according to claim 1, wherein the stabilizer is a fatty acid ester of ascorbic acid.

8. In a process for the preparation of a stable extract containing about 0.1% to 2% Hyperforin wherein *Hypericum perforatum* L. plant material is extracted with pharmaceutical inorganic or organic solvents or mixtures thereof, with the proviso that the solvents are not oily extraction agents, the improvement comprising adding a stabilizer selected from the group consisting of organic thiol compounds, ascorbic acid and derivatives thereof, either during or after the preparation of the extract, in an amount sufficient to stabilize the Hyperforin.

9. A Process according to claim 8, wherein the plant material is fresh plant material.

10. A Process according to claim 8, wherein the plant material is dried plant material.

11. A Process according to claim 8, wherein the stabilizer is cysteine.

12. A Process according to claim 8, wherein the stabilizer is glutathione.

13. A Process according to claim 8, wherein the stabilizer is asorbic acid.

14. A Process according to claim 8, wherein the stabilizer is a fatty acid ester of ascorbic acid.

15. A Process according to claim 8, wherein the stabilizer is added in a concentration of 0.01% to 5%, based on the extract.

16. A Process according to claim 8, wherein a solvent is used for the extraction.

17. A Process according to claim 8, wherein the solvent used for extraction is selected from the group consisting of aqueous ethanol, aqueous methanol, alkanes having about 5–8 carbon atoms, liquid carbon dioxide and supercritical carbon dioxide.

18. A Process according to claim 8, wherein the stabilizer is added after drying the extract solution.

19. A Process according to claim 8, wherein the stabilizer is added only to the dry extract together with conventional pharmaceutical additives.

20. A Process according to claim 8, wherein the process is carried out in the absence of light.

21. A pharmaceutical composition containing an extract according to claim 1 and conventional pharmaceutical additives for the treatment of depression and psychovegetative disorders.

22. The process according to claim 8, wherein the stabilizer is added in a concentration of 0.2% to 1% based on the extract.

23. The process according to claim 8, wherein the process is carried out in the absence of oxygen.

24. The process according to claim 8, wherein the process is carried out in the absence of light and oxygen.

25. A stable composition comprising
   (a) Hyperforin extracted from *Hypericum perforatum* L. using water and methanol or ethanol, the amount of hyperforin being from about 0.1% to 2%; and
   (b) an amount of a stabilizer selected from the group consisting of of organic thiol compounds, ascorbic acid, ascorbic acid derivatives, and mixtures thereof effective to stabilize the Hyperforin against decomposition or degradation.

26. A plant extract comprising
   (a) about 0.1% to 2% of hyperforin; and
   (b) an amount of a stabilizer selected from the group consisting of of organic thiol compounds, ascorbic acid, ascorbic acid derivatives, and mixtures thereof effective to stabilize the Hyperforin against decomposition or degradation, the hyperforin being stable in the composition for at least 12 months.

27. A pharmaceutical composition containing an extract according to claim 2 and conventional pharmaceutical additives for the treatment of depression and psychovegetative disorders.

28. A pharmaceutical composition containing an extract according to claim 3 and conventional pharmaceutical additives for the treatment of depression and psychovegetative disorders.

29. A pharmaceutical composition containing an extract according to claim 4 and conventional pharmaceutical additives for the treatment of depression and psychovegetative disorders.

30. A pharmaceutical composition containing an extract according to claim 6 and conventional pharmaceutical additives for the treatment of depression and psychovegetative disorders.

31. A pharmaceutical composition containing an extract according to claim 7 and conventional pharmaceutical additives for the treatment of depression and psychovegetative disorders.

* * * * *